United States Patent
Kristensen

(10) Patent No.: US 7,223,293 B2
(45) Date of Patent: May 29, 2007

(54) PROSTHESIS SET

(75) Inventor: Tomm Kristensen, Rindabu (NO)

(73) Assignee: Otto Bock Healthcare Products GmbH, Vienna (AT)

( * ) Notice: Subject to any disclaimer, the term of this patent is extended or adjusted under 35 U.S.C. 154(b) by 0 days.

(21) Appl. No.: 10/500,927

(22) PCT Filed: Jan. 20, 2003

(86) PCT No.: PCT/NO03/00017

§ 371 (c)(1),
(2), (4) Date: Feb. 2, 2005

(87) PCT Pub. No.: WO03/065938

PCT Pub. Date: Aug. 14, 2003

(65) Prior Publication Data

US 2005/0119755 A1    Jun. 2, 2005

(30) Foreign Application Priority Data

Jan. 18, 2002    (NO) .................................. 20020273

(51) Int. Cl.
*A61F 2/60* (2006.01)
*A61F 2/80* (2006.01)
(52) U.S. Cl. ............................................... 623/32
(58) Field of Classification Search .................. 623/32, 623/27, 33, 39, 43, 47, 30–31, 23.44, 57–65
See application file for complete search history.

(56) References Cited

U.S. PATENT DOCUMENTS

| | | | | |
|---|---|---|---|---|
| 3,947,897 A | * | 4/1976 | Owens ..................... | 623/11.11 |
| 4,143,426 A | * | 3/1979 | Hall et al. ..................... | 623/53 |
| 4,158,895 A | * | 6/1979 | Frosch et al. .................. | 606/60 |
| 5,041,137 A | * | 8/1991 | Nemoshkalov ............. | 128/898 |
| 5,405,405 A | * | 4/1995 | Love ........................... | 623/37 |
| 5,980,576 A | * | 11/1999 | Graf et al. .................... | 623/33 |
| 6,406,499 B1 | * | 6/2002 | Kania ........................... | 623/36 |
| 6,425,925 B1 | * | 7/2002 | Grundei ........................ | 623/32 |
| 6,482,238 B1 | * | 11/2002 | Grundei ........................ | 623/32 |

(Continued)

FOREIGN PATENT DOCUMENTS

DE           808974     *    7/1951    ................... 623/38

(Continued)

OTHER PUBLICATIONS

William Hall, MD, A future prosthetic limb device, Journal of Rehabilitation Research and Development vol. 22 No. 3 BPR 10-42, pp. 99-102.*

(Continued)

*Primary Examiner*—Alvin J. Stewart
(74) *Attorney, Agent, or Firm*—Ladas and Parry LLP

(57) ABSTRACT

Prosthesis set (1) for persons with amputated limbs/stumps (10) where the prosthesis set consists of an anchoring part (2) arranged internally in a remaining marrow bone (11) and an external prosthesis (7). The anchoring part (2) has a bolt-like design with a stem (3) and an expanded head (4) in one end, wherein the stem (3) can be inserted and anchored in the remaining marrow bone (11). The expanded head (4) forms a subcutaneous termination of the marrow bone (11) and a local expansion (12) at the end (10) of the amputated limb. The external prosthesis (7) has an internal design (8) adapted to the local expansion.

20 Claims, 3 Drawing Sheets

U.S. PATENT DOCUMENTS

Figure 1:
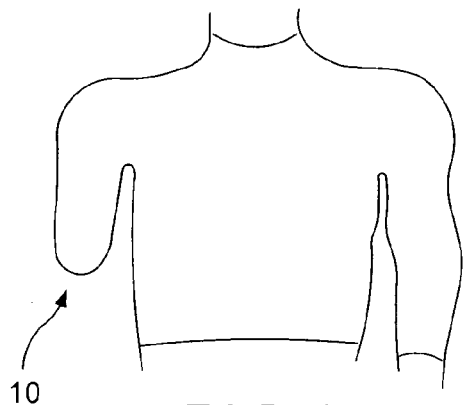

| | | | |
|---|---|---|---|
| 6,485,522 B1 * | 11/2002 | Grundei | 623/38 |
| 6,709,466 B1 * | 3/2004 | Grundei | 623/32 |
| 6,827,343 B2 * | 12/2004 | Skiera | 267/154 |
| 6,843,808 B2 * | 1/2005 | Grundei | 623/32 |
| 6,869,450 B2 * | 3/2005 | Grundei | 623/32 |
| 6,936,073 B2 * | 8/2005 | Karason | 623/37 |

FOREIGN PATENT DOCUMENTS

| | | |
|---|---|---|
| DE | 31 25 268 | 1/1983 |
| DE | 43 38 746 | 5/1995 |
| DE | 94 00 720 | 6/1995 |
| JP | 2005-34257 A * | 7/2003 |
| WO | 01/05335 | 1/2001 |

OTHER PUBLICATIONS

English Abstract of DE 4338746 Dated May 18, 1995.
English Abstract of WO 01/05335 Dated Jan. 25, 2001.

* cited by examiner

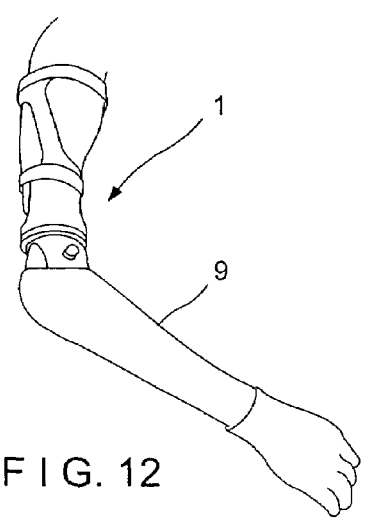
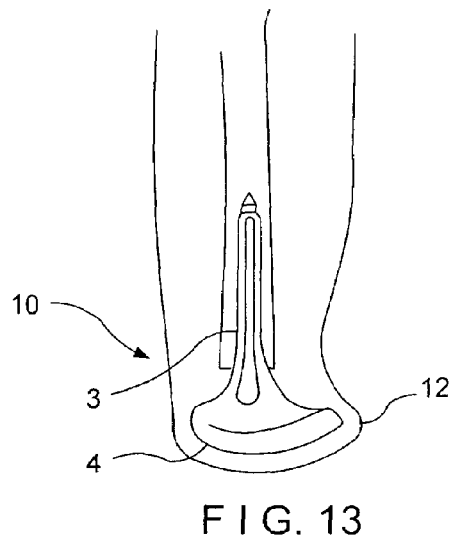
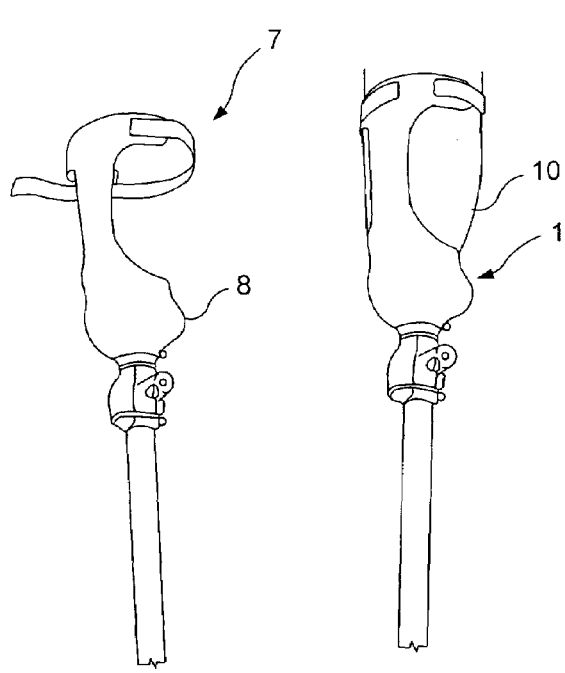
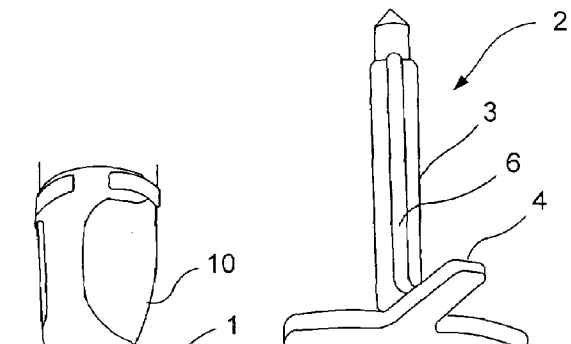
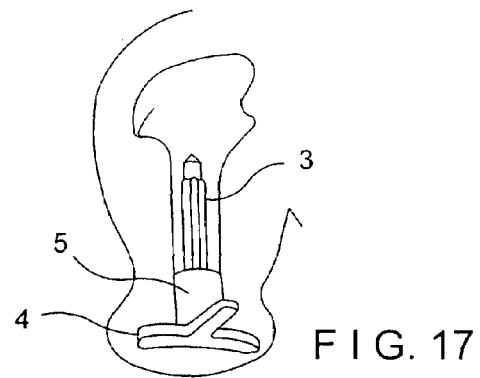
FIG. 12
FIG. 13
FIG. 14
FIG. 15
FIG. 16
FIG. 17

PROSTHESIS SET

The present invention relates to a prosthesis set for persons with amputated limbs/stumps where the prosthesis set consists of an anchoring part arranged internally in a remaining marrow bone and an external prosthesis.

Traditionally, exogenous prostheses are for example for upper arm amputees fastened to a person by vacuum or straps etc. that are fastened around the persons upper torso, i.e. neck and shoulders. Such prostheses are thus very bulky and cumbersome in use, uncomfortable and offer limited movement for the person using them. Poor anchoring of the prosthesis sleeve also reduces movement and feeling with the prosthesis. The person using the prosthesis often experiences problems with wear and tear, back problems, neck problems, problems with sweat, strangulation etc. Another problem with such prostheses is that pressure forces from the prosthesis against the end of the amputated bone can cause extensive pain, and in the worst case the bone stump can penetrate through the skin at the contact point with the prosthesis.

DE 3 125 268 A1 solves the problem of absorbing the pressure forces described above by having a bolt inserted into the end of the bone to absorb the pressure forces and functions like a "shock absorbing cushion". This publication does not, however, contribute to improving the anchoring of an exogenous prosthesis.

There is today another solution that offers a better prosthesis function than the solution described above. In this connection reference is made to DE 4 338 746 A1, which comprises a prosthesis set for persons with amputated limbs/stumps. The prosthesis set consists of an anchoring part arranged internally in a remaining marrow bone and an external prosthesis. The anchoring part or fastening arrangement to the bone extends through the skin and the solution is not therefore a closed (subcutaneous) system. The anchoring part or the titanium bolt penetrates the skin and this creates a great risk of infection for the patient. The risk of infection means the patient must daily disinfect the wound (which will never heal) in the area where the titanium bolt penetrates the skin. The risk of infection further implies that only a small number of patients qualify for such an implant. Another weakness with a non-closed system is that the patient experiences discomfort due to the transfer of heat/cold. The titanium bolt, which is exposed to the outer environment, transfers heat/cold into the tube skeleton. Some patients are also very sensitive to jolts, since the jolts spread through the bolt and into the tube skeleton. There are no soft parts between the stump and the exogenous prosthesis that can absorb these forces. This solution requires several surgical operations with 6–9 months intervals, which puts great strain on the patient.

One objective of the present invention is to create a prosthesis set for persons with amputated limbs/stumps where the prosthesis sleeve is better anchored to the amputated limb or stump, thus improving the function of the prosthesis.

Another objective is that the prosthesis shall have a simple fastening locally to the amputated stump, and that the prosthesis can be anchored distally to the stump. Such an anchoring of the prosthesis will increase the degree of freedom, i.e. mobility is improved.

A third objective is that the user of the prosthesis shall be able to put weight on the end of the prosthesis as well as transfer torsion forces from the stump to the prosthesis.

A fourth objective is that the prosthesis set shall be able to be applied to all amputated limbs, for example humerus, femur, tibia, fibula, ulna, radius, etc.

A fifth objective of the invention is that it shall be possible to extend the amputated stump to obtain the most ideal stump length for fastening an external prosthesis.

The objectives of the invention are achieved by a prosthesis set for persons with amputated limbs/stumps where the prosthesis set consists of an anchoring part arranged internally in a remaining marrow bone and an external prosthesis characterised by that the anchoring part has a bolt-like shape with a stem and an expanded head at one end, wherein the stem can be inserted and anchored in the remaining marrow bone and that the expanded head forms, respectively, a subcutaneous termination of the marrow bone and a local expansion at the amputated limb's end and that the external prosthesis has an internal shape adapted to the local expansion.

Preferred embodiments of the prosthesis set are further described in the claims 2–9.

Figure 2:
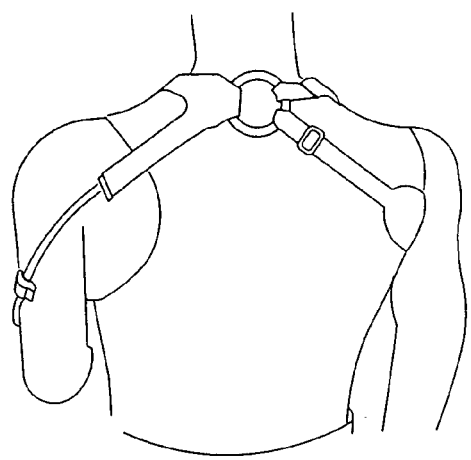
Figure 3:
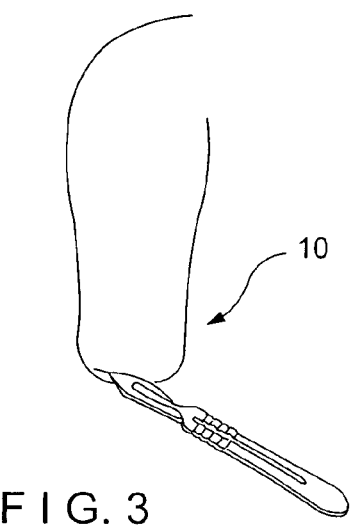
Figure 4:
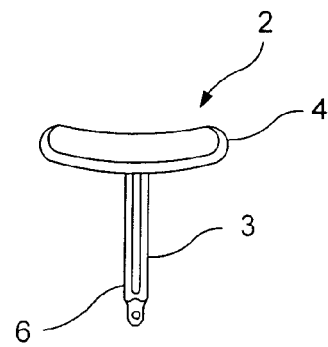
Figure 5:
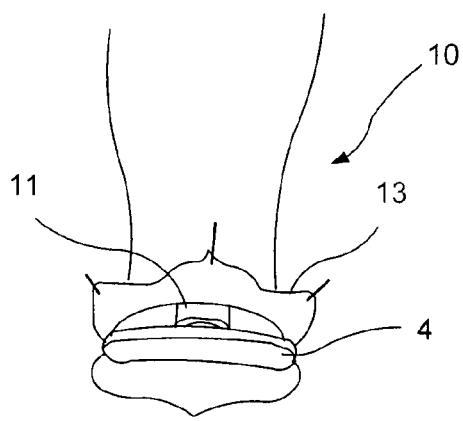
Figure 6:
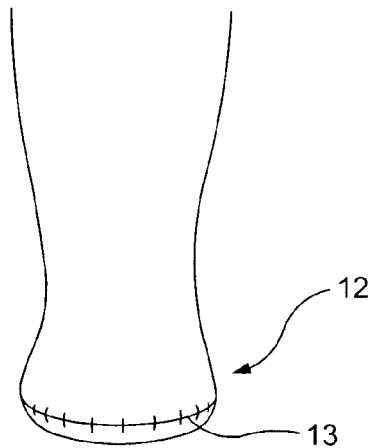
Figure 7:
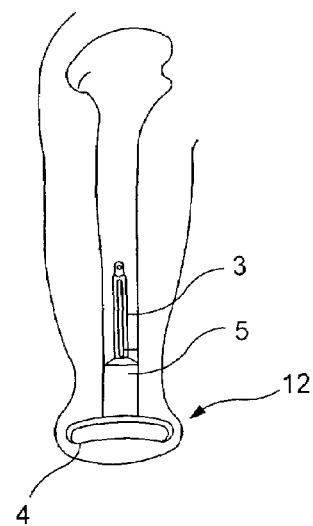
Figure 8:
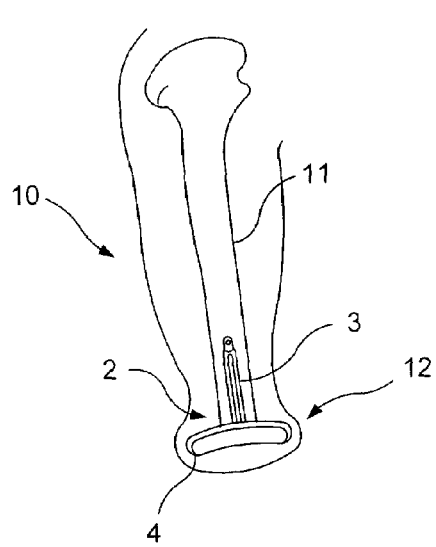
Figure 9:
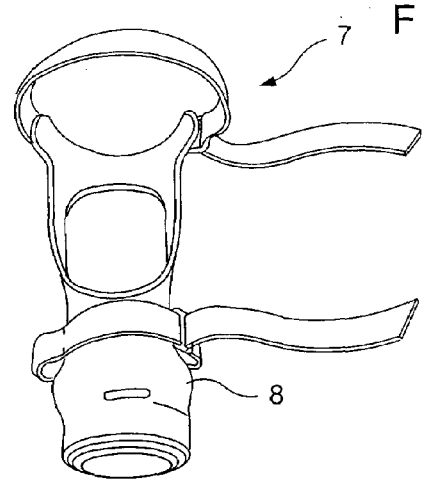
Figure 10:
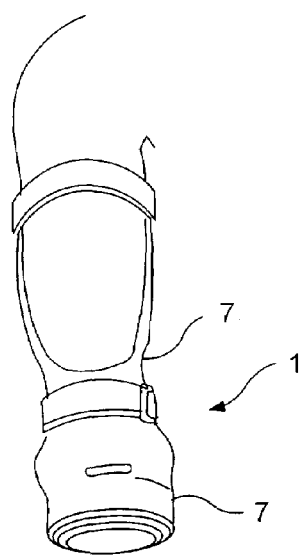
Figure 11:
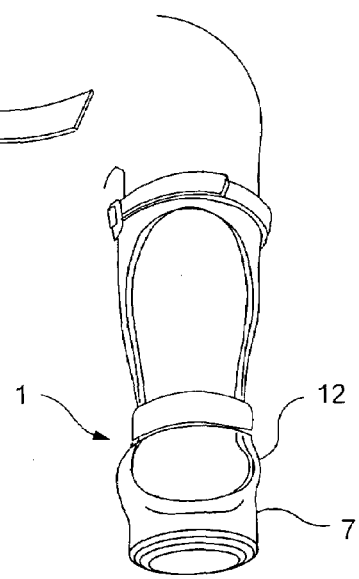

Preferred embodiment examples of the present invention will now be explained with reference to the Figures, where FIG. 1 shows a person with an amputated upper arm, FIG. 2 shows the person from FIG. 1 equipped with a traditional prosthesis with straps, FIG. 3 shows the amputated upper arm from FIG. 1, and illustrates the first step in a method for implanting an anchoring part for a prosthesis set according to the present invention, FIG. 4 shows the anchoring part itself, FIG. 5 shows the anchoring part inserted into the upper arm bone of the person in FIG. 1, FIG. 6 shows a termination of the person's upper arm after the anchoring part has been inserted, FIG. 7 shows schematically the anchoring part from FIGS. 4 and 5 inserted into the upper arm bone, FIG. 8 shows a second embodiment of the anchoring part inserted into a person's marrow bone, FIG. 9 shows the external prosthesis of the prosthesis set according to the present invention, FIG. 10 shows the prosthesis set arranged on the person's upper arm with an anchoring part inserted. The person is here seen from the front, FIG. 11 shows the external prosthesis in FIG. 10 now seen from behind, FIG. 12 shows the prosthesis set in FIG. 11 with the under arm attached, FIG. 13 shows a third embodiment of an anchoring part according to the invention, now arranged internally in a thighbone, FIG. 14 shows an external prosthesis for a thighbone, FIG. 15 shows the external prosthesis arranged on the thighbone in FIG. 13, FIG. 16 shows a fourth embodiment of the anchoring part according to the present invention, and FIG. 17 shows a fifth embodiment of the connection part inserted into a person's upper arm.

With reference to the Figures above, it must be noted that the same reference numbers are used to designate the corresponding parts throughout the different embodiments of the invention.

FIG. 1 shows a person with an amputated upper arm 10, and FIG. 2 shows the person with a traditional exogenous prosthesis. As FIG. 2 shows, the prosthesis covers the whole upper arm, parts of the shoulder and is further fastened by straps around the neck and shoulders. The prosthesis is large and bulky and has a fastening arrangement that reduces the person's mobility and feeling with the prosthesis. In addition, it is apparent that the user could have problems with wear, sweat, etc.

FIG. 3 shows a first step in a method for implanting an anchoring part 2 belonging to the prosthesis set 1 according to the present invention. A surgical operation 13 is carried out at the end of the amputated upper arm 10 and the amputated end of the marrow bone (the upper arm bone) 11 is uncovered. The anchoring part 2 with stem 3 and an expanded head 4 according to FIG. 4 is inserted into the bone of the upper arm or the marrow bone 11. Before the insertion of the anchoring part 2 the inside of the marrow bone 11 will be drilled out and adjusted to the anchoring part 2 which again will be cemented internally in the marrow bone 11. The stem 3 of the anchoring part will be arranged with one or more longitudinal grooves 6, preferably for applying cement filling. FIG. 6 shows the amputated upper arm 10 with inserted anchoring part 2. As this FIG. shows, the expanded head 4 of the anchoring part 2 will produce a local expansion 12 at the amputated limb's end 10. This expansion bulge 12 will enable a very good anchoring for an external prosthesis 7 according to the present invention. FIG. 7 shows schematically the anchoring part 2 inserted and cemented inside the marrow bone 11 and illustrates clearly that the expanded head 4 forms a subcutaneous termination of the marrow bone 11 and a local expansion 12 at the amputated limb's end. Head 4 of the anchoring part is here plate shaped and slightly curved.

FIG. 8 shows a second embodiment of the anchoring part 2, now with a local expansion 5 towards the expanded head 4. This second embodiment of the anchoring part 2 is used in cases where it is necessary to extend the marrow bone 11 to achieve a better fixture of the external prosthesis 7. This will be, for example, in cases where the upper arm 10 is amputated higher up towards the armpit. FIG. 9 shows the external prosthesis 7 as a part of the prosthesis set 1. The external prosthesis 7 is adapted to the amputated upper arm 10 and the local expansion bulge 12 in particular, which is a result of the implanted anchoring part 2. FIG. 10 shows the complete prosthesis set from the front and FIG. 11 shows the complete prosthesis set from behind. As can be seen from FIGS. 10 and 11, the external prosthesis 7 is significantly smaller and thus lighter and more user-friendly than the traditional prosthesis shown in FIG. 2. The local fastening of the external prosthesis 7 also contributes to increased freedom of movement and greater comfort for the user. FIG. 12 shows the prosthesis set 1 with attached operationable artificial underarm 9.

FIG. 13 shows a third embodiment of the anchoring part 2 arranged in an amputated thighbone. As the figure shows, the head 4 in particular has a completely different shape and is constructed to absorb greater pressure forces due to the great pressure shock that such a leg prosthesis involves. FIG. 14 shows an external prosthesis 7 for use in connection with the amputated thighbone incorporating the implant according to the present invention. FIG. 15 shows the complete prosthesis set 1 for a person with a leg amputated at the thigh. As FIG. 15 shows, the local expansion bulge 12 and the adapted internal design bulge 8 in the external prosthesis 7 provide a good anchoring. A good "shock-absorbing cushion" is further achieved by means of the anchoring part's expanded head 4.

FIG. 16 shows a fourth embodiment of the anchoring part 2. The head of the anchoring part now has a T-shape and is slightly curved.

FIG. 17 shows a fifth embodiment of the anchoring part 2. The anchoring part's stem 3 now has an expansion 5 nearest the head 4. This expansion 5 serves in this case as an extension of the marrow bone 11 as described in connection with FIG. 8, and would in this case be suitable for a person whose arm has been amputated well above the elbow. The extension of the upper arm bone 11 will give better grip for the external prosthesis 7 and thus increase the prosthesis function for the person.

It should be mentioned that the surgical operation will be carried out by an orthopaedist or surgeon. The implant or the anchoring part 2 is fastened to the marrow bone (tube bone) 11 by cementing, and this is a technology that is known in applications like hip joint prostheses, knee joint prostheses etc. The implanting of the anchoring part (condyle) is performed surgically, and will thus be healed in 3–4 weeks. This implies that the patient can have full use of the prosthesis set 1 already 4–6 weeks after the operation. The anchoring condyle will be produced in titanium, a material the body does not reject. Surgical steel is another material that can be used. The implant will be in a closed environment, subcutaneous, which to a great extent reduces the danger of infections and transfer of coldness.

Ultimately, it should be mentioned that the invention is not limited to the shown embodiments, in that it can be used for other amputated body parts and modifications can be adapted without leaving the idea of the invention.

The invention claimed is:

1. A prosthesis set for a person with an amputated limb, said prosthesis set comprising:
    (a) an anchoring part that is disposable in a marrow bone of the amputated limb near a stump of the limb, the anchoring part comprising a bolt-like shape with a stem and a head at one end of the stem, the stem being insertable in the marrow bone with the head disposed at an end of the marrow bone, said head having a shape such that disposition of the anchoring part in the marrow bone of the amputated limb causes a local expansion or bulge in the stump; and
    (b) a prosthesis sleeve for affixing to the amputated limb, said prosthesis sleeve comprising anchoring means, comprising a bulge corresponding to the local expansion or bulge of the limb, for receiving the local expansion or bulge of the limb and establishing a local form fitting anchorage for the prosthesis sleeve.

2. The prosthesis set according to claim 1, wherein the stem comprises an expansion adjacent the head.

3. The prosthesis set according to claim 1, wherein the stem comprises at least one longitudinal groove.

4. The prosthesis set according to claim 1, wherein the head is plate shaped.

5. The prosthesis set according to claim 4, wherein the plate shaped head is slightly curved.

6. The prosthesis set according to claim 1, wherein the head is T-shaped.

7. The prosthesis set according to claim 6, wherein the T-shaped head is slightly curved.

8. A method for anchoring a prosthesis to a person with an amputated limb, said method comprising the steps of:
    (i) providing the prosthesis set according to claim 7;
    (ii) inserting the stem of the anchoring part into a marrow bone of the amputated limb near a stump of the limb with the head of the anchoring part disposed at an end of the marrow bone, said head having a width that exceeds the width of the marrow bone in an amount such that disposition of the anchoring part in the marrow bone of the amputated limb causes a local expansion or bulge at a distal end of the stump that is wider than an adjacent proximal part of the amputated limb; and (iii) affixing the prosthesis sleeve to the amputated limb with the local expansion or bulge in the stump received in the bulge of the prosthesis sleeve to anchor the prosthesis sleeve to the amputated limb.

9. A method for anchoring a prosthesis to a person with an amputated limb, said method comprising the steps of:

(i) providing the prosthesis set according to claim 6;

(ii) inserting the stem of the anchoring part into a marrow bone of the amputated limb near a stump of the limb with the head of the anchoring part disposed at an end of the marrow bone, said head having a width that exceeds the width of the marrow bone in an amount such that disposition of the anchoring part in the marrow bone of the amputated limb causes a local expansion or bulge at a distal end of the stump that is wider than an adjacent proximal part of the amputated limb; and (iii) affixing the prosthesis sleeve to the amputated limb with the local expansion or bulge in the stump received in the bulge of the prosthesis sleeve to anchor the prosthesis sleeve to the amputated limb.

10. The method according to claim 9, wherein in step (ii) the stem is inserted into the marrow bone with the head of the anchoring part disposed transverse to the end of the marrow bone.

11. The prosthesis set according to claim 1, wherein the stem and head of the anchoring comprise titanium.

12. The prosthesis set according to claim 1, wherein the stem and head of the anchoring part comprise surgical steel.

13. The prosthesis set according to claim 1, wherein the prosthesis sleeve comprises fastening means for fastening the prosthesis sleeve to the amputated limb.

14. The prosthesis set according to claim 13, wherein the fastening means comprises strap means for adjustable affixation of the prostheses sleeve around a circumference of the amputated limb.

15. A method for anchoring a prosthesis to a person with an amputated limb, said method comprising the steps of:

(i) providing the prosthesis set according to claim 14;

(ii) inserting the stem of the anchoring part into a marrow bone of the amputated limb near a stump of the limb with the head of the anchoring part disposed at an end of the marrow bone, said head having a width that exceeds the width of the marrow bone in an amount such that disposition of the anchoring part in the marrow bone of the amputated limb causes a local expansion or bulge at a distal end of the stump that is wider than an adjacent proximal part of the amputated limb;

(iii) affixing the prosthesis sleeve to the amputated limb with the local expansion or bulge in the stump received in the bulge of the prosthesis sleeve to anchor the prosthesis sleeve to the amputated limb; and (iv) fastening the strap around the amputated limb.

16. The method according to claim 15, wherein in step (ii) the stem is inserted into the marrow bone with the head of the anchoring part disposed transverse to the end of the marrow bone.

17. A method for anchoring a prosthesis to a person with an amputated limb, said method comprising the steps of:

(i) providing the prosthesis set according to claim 1;

(ii) inserting the stem of the anchoring part into a marrow bone of the amputated limb near a stump of the limb with the head of the anchoring part disposed at an end of the marrow bone, said head having a width that exceeds the width of the marrow bone in an amount such that disposition of the anchoring part in the marrow bone of the amputated limb results in a local expansion or bulge at a distal end of the stump that is wider than an adjacent proximal part of the amputated limb; and (iii) affixing the prosthesis sleeve to the amputated limb with the local expansion or bulge in the stump received in the bulge of the prosthesis sleeve to anchor the prosthesis sleeve to the amputated limb.

18. The method according to claim 17, wherein in step (ii) the stem is inserted into the marrow bone with the head of the anchoring part disposed transverse to the end of the marrow bone.

19. The prosthesis set according to claim 1, wherein the local form fitting anchorage that is established by the anchoring means provides for a transfer of torsion forces from the stump to a prosthesis received in the prosthesis sleeve.

20. The prosthesis set according to claim 1, wherein the stem is insertable in the marrow bone with the head disposed transverse to the end of the marrow bone.

* * * * *